(12) United States Patent
Tadini D'annolfo et al.

(10) Patent No.: US 11,666,518 B2
(45) Date of Patent: *Jun. 6, 2023

(54) COSMETIC ANTI-BLEMISH COMPOSITION, USE OF THE COMPOSITION AND METHOD FOR ANTI-BLEMISH TREATMENT

(71) Applicant: Natura Cosméticos S.A., São Paulo (BR)

(72) Inventors: Kassandra Tadini D'annolfo, São Paulo (BR); Priscila Carollo Moncayo, São Paulo (BR); Eduardo Alexandre De Oliveira Reis, São Paulo (BR); Fabiana Paes, São Paulo (BR); Ricardo Augusto Santos De Oliveira, São Paulo (BR); Daniela Zimbardi, São Paulo (BR)

(73) Assignee: Natura Cosméticos S.A., São Paulo (BR)

( * ) Notice: Subject to any disclaimer, the term of this patent is extended or adjusted under 35 U.S.C. 154(b) by 165 days.

This patent is subject to a terminal disclaimer.

(21) Appl. No.: 16/312,409

(22) PCT Filed: May 24, 2017

(86) PCT No.: PCT/BR2017/050130
§ 371 (c)(1),
(2) Date: Dec. 21, 2018

(87) PCT Pub. No.: WO2018/032075
PCT Pub. Date: Feb. 22, 2018

(65) Prior Publication Data
US 2019/0240127 A1 Aug. 8, 2019

(30) Foreign Application Priority Data
Aug. 17, 2016 (BR) .................... 102016019117-3

(51) Int. Cl.
| | | |
|---|---|---|
| *A61K 8/34* | (2006.01) | |
| *A61Q 19/08* | (2006.01) | |
| *A61K 8/9789* | (2017.01) | |
| *A61K 8/9794* | (2017.01) | |
| *A61K 8/73* | (2006.01) | |
| *A61K 8/92* | (2006.01) | |

(52) U.S. Cl.
CPC .............. *A61K 8/347* (2013.01); *A61K 8/345* (2013.01); *A61K 8/9789* (2017.08); *A61K 8/9794* (2017.08); *A61Q 19/08* (2013.01); *A61K 8/73* (2013.01); *A61K 8/92* (2013.01); *A61K 2800/522* (2013.01)

(58) Field of Classification Search
None
See application file for complete search history.

(56) References Cited

U.S. PATENT DOCUMENTS

| | | | |
|---|---|---|---|
| 9,714,376 B2 * | 7/2017 | Yang | A61K 8/042 |
| 2002/0035046 A1 * | 3/2002 | Lukenbach | A61K 8/85 510/122 |
| 2008/0260806 A1 * | 10/2008 | Miller | A61K 8/9794 424/443 |
| 2008/0260869 A1 * | 10/2008 | Faller | A61K 8/347 424/736 |
| 2009/0117061 A1 | 5/2009 | Gross | |
| 2010/0233301 A1 * | 9/2010 | Cheng | A61K 8/9728 424/728 |

FOREIGN PATENT DOCUMENTS

| | | |
|---|---|---|
| JP | 2001/322940 | 11/2001 |
| JP | 2003/055190 | 2/2003 |
| WO | WO 2012/168894 | 12/2012 |
| WO | WO 2015/031971 | 3/2015 |

OTHER PUBLICATIONS

Eissa and Diamandis "Human tissue kallikreins as promiscuous modulators of homeostatic skin barrier functions." Biol Chem. Jun. 2008 389(6):669-80.
Kanitakis "Anatomy, histology and immunohistochemistry of normal human skin." Eur J Dermatol. Jul.-Aug. 2002;12(4):390-9; quiz 400-1.
Anderegg et al., "More than just a filler—the role of hyaluronan for skin homeostasis." Exp Dermatol. May 2014;23(5):295-303.
Li WH et al. "IL-11, IL-1α, IL-6, and TNF-α are induced by solar radiation in vitro and may be involved in facial subcutaneous fat loss in vivo." J Dermatol Sci. Jul. 2013;71(1):58-66.
International Search Report and Written Opinion for International Application No. PCT/BR2017/050130 dated Aug. 17, 2017, 9 pages.
Kanitakis, Jean, "Anatomy, histology and immunohistochemistry of normal human skin," European Journal of Dermatology, 12(4):390-401, (2002).

* cited by examiner

*Primary Examiner* — David J Blanchard
*Assistant Examiner* — Sarah J Chickos
(74) *Attorney, Agent, or Firm* — Alston & Bird LLP

(57) ABSTRACT

The present invention relates to cosmetic anti-blemish compositions, in the form of a serum, which are particularly useful in treatments for restoring facial firmness and elasticity (loss of tone).

6 Claims, 2 Drawing Sheets

COSMETIC ANTI-BLEMISH COMPOSITION, USE OF THE COMPOSITION AND METHOD FOR ANTI-BLEMISH TREATMENT

FIELD OF THE INVENTION

The present invention relates to anti-aging cosmetic compositions in the form of a serum, which are particularly useful in a treatment to restore facial firmness and elasticity (sagging).

PRIOR ART

Over time the skin of the face loses firmness and elasticity and the resulting effects are sagging and loss of firmness, which are mainly perceived by loss of facial contour.

Skin firmness can be measured by a decrease in the resistance that it offers to being "pulled", characterizing itself as a more vulnerable tissue to deformations. On the other hand, increased sagging can be perceived by the difficulty that it presents, when subjected to deformation (being "pulled"), to return to its initial state, being characterized by a delay in returning or even by not returning to it.

Concerning skin firmness and elasticity, the main layer involved in this process is the dermis, which is located just below the epidermis and consists primarily of fibers, non-fibrous proteins and some cell types. The main cell of the dermis is the fibroblast, and the set of fibers and non-fibrous proteins of the dermis is designated dermal matrix (Bolognia 1989). The dermis matrix is composed primarily of collagen, a protein fiber that accounts for about 98% of the dermis weight, as well as elastic fibers, microfibrils and non-fibrillar proteins, such as hyaluronic acid, which together contribute to firmness, resistance, strength and elasticity of the skin. The epidermis, the uppermost and outermost layer of the skin, is basically formed by a brick-and-cement-like structure, wherein bricks are dead cells filled with keratin and lipids are the cement that ensures cohesion of said layer, which is located at the air interface and contributes to the barrier and protection function of the skin (Fuchs and Byrne 1994; Candi et al 2005; Proksch et al 2008). The process of skin renewal is very important to ensure a better protective barrier function and also a more homogeneous and even appearance of the skin.

Dermis and epidermis lie on a fat layer designated hypodermis, which are deep tissues that act as a skin support layer helping to maintain the shape and harmony of the facial contour.

The main systems and processes in the skin that affect firmness and elasticity are:

- Reduction in the number and activity of fibroblasts, which are dermal cells responsible for producing extracellular matrix fibers and proteins, which in turn results in several changes in the structure and function of the dermis (Chan et al 1994);
- With aging the production speed and the amount of collagen molecules produced by fibroblasts are markedly reduced. It starts by a reduction in collagen precursors and then proceeds with a continuous rupture of the existing fibers at a rate of approximately 1% per year from the age of 30 (Bolognia et al. 1989);
- Over time, there is an increase in the skin of the production of enzymes (collagenases) that break down and rupture pre-existing collagen fibers (Bolognia 1989; Chan et al 1994) and the biological glycation process that immobilizes and stiffens proteins of the dermis, mainly collagen, for being a large and highly durable protein;
- An increase in inflammatory processes and reactive oxygen species accelerate molecular aging, resulting in loss of the ability of the skin to deform, reduced tensor power of the skin and increased wrinkles and skin fragility (Monnier, 2005);
- The elastic system of the skin formed by elastin fibers and auxiliary proteins reaches its molecular peak during the second decade of life. However, from the age of 30, this system begins to undergo progressive degeneration reaching the level of preventing the remaining fibers from functioning at an age close to 70 (Nakamura et al., 2002; Yamanouchi et al., 2012);
- Aging and excessive UV irradiation cause an increased production in the dermis of enzymes such as elastases and matrix metalloproteinases (MMPs), which when active, degrade and break the fibers of the dermal matrix such as collagen and elastin;
- Epidermal turnover decreases by up to 50% in the period from 20 to 70 years (Eissa and Diamandis 2008);
- The lower cell differentiation rate in the epidermis reduces the rate of skin barrier renewal, and the lower number of cell junctions reduce cell cohesion. The result is a more brittle, flaky epidermis that loses more water (dehydrates) and can absorb unwanted substances (Chan 1994) resulting in dryness and a rough and coarse appearance of dehydrated skin (Kanitakis 2002);
  - Hyaluronic acid interacts with fibers and proteins from the matrix of the dermis and by binding to collagen and elastin fibers, they act to optimize the formation of fibers and protect them from the action of enzymes involved in their degradation, contributing to elasticity and firmness of the skin (EZURA et al 2013, ANDEREGG et al 2014); and
  - According to Li W H et al, skin exposure to solar radiation may induce the production of inflammatory cytokines by keratinocytes and fibroblasts and they may inhibit the differentiation process of hypodermal preadipocytes, which would affect functionality of the fat tissue and accordingly firmness, elasticity and facial support.

To protect and restore the skin, it is not sufficient to treat just a single cause of the problem, but to act on all of them. To that end, treatment for firmness and elasticity must act on the maintenance, stimulation and more effective regulation of the production of substances that constitute the skin, more intense cell renewal, recovery of natural humidity combined with a stronger prevention against the main aggression mechanisms.

Cosmetic compositions effective to provide facial firmness and elasticity are still desired.

BRIEF DESCRIPTION OF THE FIGURES

The graph of FIG. 1 shows the mean values of the Ur/Ue parameter obtained throughout the study (Mean±SD, n=26).

The graph of FIG. 2 shows the mean values of the Ur/Uf parameter obtained throughout the study (Mean±SD, n=26).

Figure 3:
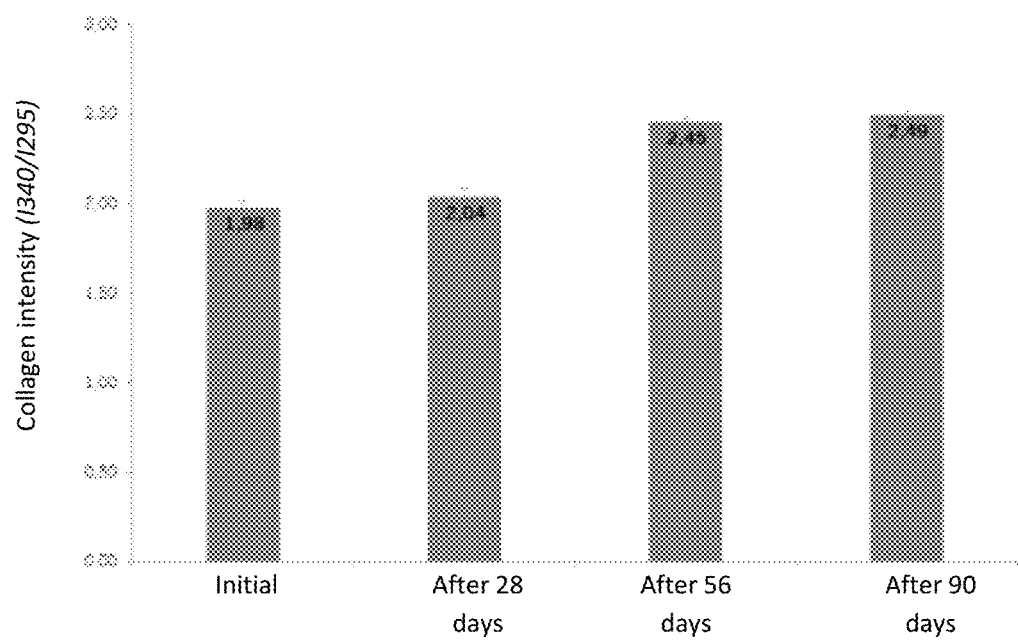

The graph of FIG. 3 shows mean values of collagen intensity, I340/I295 versus time. Mean±standard deviation, n=20.

DESCRIPTION OF THE INVENTION

The present invention relates to anti-aging cosmetic compositions in the form of a serum, which are particularly useful in a treatment to restore facial firmness and elasticity (sagging).

Surprisingly, the compositions according to the present invention exhibit effective results:
Immediately: immediate lifting effect;
After 7 days: they enhance collagen production by up to 8×2 and restore the facial contour;
After 15 days: they smooth wrinkles, revitalize and lighten the skin;
After 30 days: they restore firmness.

"Serum", in the context of the present invention, means compositions having a distinct texture, characterized by lightness during application, fluid appearance and by comprising higher concentrations of active ingredients than common cosmetic treatments, forming a polymeric film on the skin surface, which when dried promotes an immediate tensor effect facilitating permeation of active ingredients and an interaction with the skin to stimulate and protect its main mechanisms, cells and fibers that guarantee skin support, firmness and elasticity.

The anti-aging cosmetic compositions according to the present invention are provided in the form of a serum comprising:
a) at least one antioxidant;
b) at least one humectant;
c) at least one active ingredient;
d) at least one emulsifier; and
e) cosmetically acceptable carriers.

The antioxidant is selected from the group consisting of butylated hydroxytoluene (BHT), tocopherol acetate or natural plant extracts, or mixtures thereof, particularly butylated hydroxytoluene (BHT);

The humectant is selected from the group consisting of glycerol, glycols, sorbitol, mannitol or mixtures thereof, particularly glycerol;

The active ingredient is selected from the group consisting of a mixture of *Paeonia albiflora* root extract/phenoxyethanol/ethyl hexylglycerine, a mixture of *Secale Cereale* extract/penethylene glycol, *Avena Sativa* extract, *Hymenaea courbaril* extract, *Schinus terebinthifolius* extract, a mixture of *Casearia sylvestris*/silica, acetyl tetrapeptide-2, a mixture of sodium cocoyl amino acids/sarcosine/potassium aspartate/magnesium aspartate/propylene glycol, *Cichorium intybus* extract, or mixtures thereof, particularly the mixture of *Paeonia albiflora* root extract/phenoxyethanol/ethylhexylglycerin, mixture of *Secale Cereale* extract/penethylene glycol, *Avena Sativa* extract, *Hymenaea courbaril* extract, *Schinus terebinthifolius* extract, a mixture of *Casearia sylvestris*/silica, or mixtures thereof;

The emulsifier is selected from the group consisting of PEG-40 hydrogenated castor oil, glyceryl citrate, potassium cetyl phosphate, PEG-100, acrylates, xanthan gum, cetearyl alcohol, mixture of glyceryl stearate/PEG-100, or mixtures thereof, particularly PEG-40 hydrogenated castor oil.

Cosmetically acceptable carriers may be selected from compounds known in the art.

Exemplary carriers are: solvents, preservatives (such as phenoxyethanol and iodopropynyl butylcarbamate), perfumes/fragrances (such as pataqueira essential oil), polymer neutralizers, chelating agents (such as disodium EDTA), pH adjusting agents, among others.

The compositions according to the present invention may further comprise a viscosity donor selected from xanthan gum, carbopol, a mixture of hydroethylacrylate/sodium acryloyldimethyltaurate copolymer/squalane/polysorbate 60, or mixtures thereof. In particular, the viscosity donor is xanthan gum.

The cosmetic compositions according to the present invention act on 11 major mechanisms responsible for restoring skin firmness and elasticity, acting on 11 mechanisms:
1. Increase in collagen production by up to 8×*;
2. Formation of a tensor film on the surface of the skin;
3. Reinforcement of the skin supporting tissue;
4. Restores natural hydration;
5. Elastin stimulation;
6. Hyaluronic acid stimulation;
7. Cell renewal;
8. Elastin protection;
9. Collagen protection;
10. Tensor effect on the deeper layers of the skin; and
11. Protection of the supporting fibers.

Another object of the present invention consists of the use of the cosmetic compositions in an anti-aging treatment, particularly to restore firmness and elasticity of facial skin.

Still another object of the present invention is an anti-aging treatment method as well as a method for restoring firmness and elasticity of facial skin, which comprises applying a cosmetically effective amount of the composition according to the present invention at least once a day.

The following examples, without any limitation, illustrate the anti-aging cosmetic compositions according to the present invention, which surprisingly provide an immediate and prolonged effect, as explained herein.

EXAMPLES

Example 1. Composition According to the Present Invention

The following table illustrates the cosmetic compositions according to the present invention.

TABLE 1

| Anti-aging cosmetic compositions | | |
|---|---|---|
| Ingredient | Example A | Example B |
| Water/*Paeonia albiflora* extract/phenoxyethanol/ethylhexyl glycerin | 2.00 | 1.50 |
| Water/*Secale Cereale* Extract/Penthylene Glycol | 4.00 | 6.00 |
| aqua | 80.63 | 82.11 |
| *Avena Sativa* Extract/Water | 4.00 | 2.00 |
| Butylated Hydroxytoluene (BHT) | 0.05 | 0.05 |
| Disodium EDTA | 0.10 | 0.10 |
| Fragrance | 0.20 | 0.20 |
| Glycerin (glycerol) | 5.00 | 4.00 |
| *Hymenaea courbaril* Extract | 0.50 | 0.70 |
| Iodopropynyl Butylcarbamate | 0.09 | 0.08 |
| Pataqueira essential oil | 0.001 | 0.001 |
| PEG-40 Hydrogenated Castor Oil | 1.00 | 1.50 |
| Phenoxyethanol | 0.80 | 0.70 |
| *Schinus terebinthifolius* Extract | 0.03 | 0.01 |
| Water/*Casearia sylvestris* Extract/Silica | 0.10 | 0.05 |
| Xanthan gum (Keltrol SFT) | 1.50 | 1.00 |
| TOTAL | 100.00 | 100.00 |

Example 2. Evaluation of the Increase in Skin Firmness and Elasticity by Cutometry 26 survey participants have completed the study and their average age was: 51±8 years.) There were no reports or evidence of adverse reaction during the study.

The product was applied twice a day, once in the morning and once at night, on the forearm identified with a satin ribbon, by massaging it until completely absorbed.

The methodology consisted of evaluating the increase in skin firmness and elasticity through cutometry measurements (Cutometer® MPA-580 and Multiprobe Adapter MPA-580, CKeletronics, Germany) performed in the beginning of the study, after 30 minutes from the first application and after 28 and 56 days of home use of the product under investigation. Cutometry measurements were performed on the forearm region. The increase in skin firmness has been evaluated using the Ur/Ue parameter (R5) and the increase in skin elasticity was evaluated using the Ur/Uf parameter (R7).

Skin firmness has been assessed using the Ur/Ue parameter. Ur/Ue parameter is the ratio between immediate retraction and immediate skin deformation and corresponds to the biological elasticity.

Increased skin firmness is evidenced by an increase in the Ur/Ue parameter that reflects an improvement of properties of the elastic fibers and collagen.

Skin elasticity was evaluated using the Ur/Uf parameter, which consists of the ratio between immediate retraction and total skin deformation, including the viscous part of skin deformation, and corresponds to biological elasticity.

Increased skin elasticity is evidenced by the increase in the Ur/Uf parameter that reflects an improvement of the elastic fiber properties.

Based on the mean values of the Ur/Ue parameter, the percent increase in skin firmness (% AF) is calculated according to equation 1. % AFti=100*(Ur/Ueti−Ur/Uet0)/Ur/Uet0 (Equation 1) wherein: % AFti=percent increase in firmness; Ur/Ueti=mean Ur/Ue parameter values obtained after i days of study (i=30 minutes, 28 and 56 days); Ur/Urt0=mean Ur/Ue parameter values obtained in the beginning of the study (baseline).

Based on the mean values of the Ur/Uf parameter, the percent increase in skin elasticity (% AE) is calculated according to equation 2. % AEti=100*(Ur/Uf ti−Ur/Uf t0)/Ur/Uf t0 (Equation 2) wherein: % AEti=percent increase in elasticity; Ur/Ufti=mean Ur/Uf parameter values obtained after i days of study (i=30 minutes, 28 and 56 days); Ur/Uft0=mean Ur/Uf parameter values obtained in the beginning of the study (baseline).

The significance of the increase in skin firmness is assessed by applying a bimodal, paired Student's t-test method based on a 95% confidence interval to the basal mean values of the Ur/Ue parameter in relation to the values obtained after i days of use; i=30 minutes, 28 and 56 days. The proper result is achieved when Ur/Ueti is significantly higher than Ur/Uet0 ($P<0.05$) indicating an increase in skin firmness.

The significance of increased skin elasticity is assessed by applying the bimodal, paired Student's t-test method, based on a 95% confidence interval, to the basal mean values of the Ur/Uf parameter in relation to values obtained after i days of use; i=30 minutes, 28 and 56 days. The proper result is achieved when Ur/Ufti is significantly higher than Ur/Uf t0 ($P<0.05$) indicating an increase in skin elasticity.

According to the results, it was verified that there was a significant increase in firmness and elasticity of the forearm skin after 28 and 56 days of home use of the product under investigation.

The percent values of increase in forearm skin firmness were: 4.0% after 28 days and 9.1% after 56 days of home use.

75.0% of the survey participants exhibited increased forearm skin firmness after 28 days and 80.0% after 56 days of home use of the product being investigated.

The percent values obtained of increase in forearm skin elasticity were: 3.4% after 28 days and 6.2% after 56 days of home use.

76.9% of the survey participants exhibited increased forearm skin elasticity after 28 days and 84.6% after 56 days of home use of the product being investigated.

BRIEF DESCRIPTION OF THE FIGURES

Figure 1:
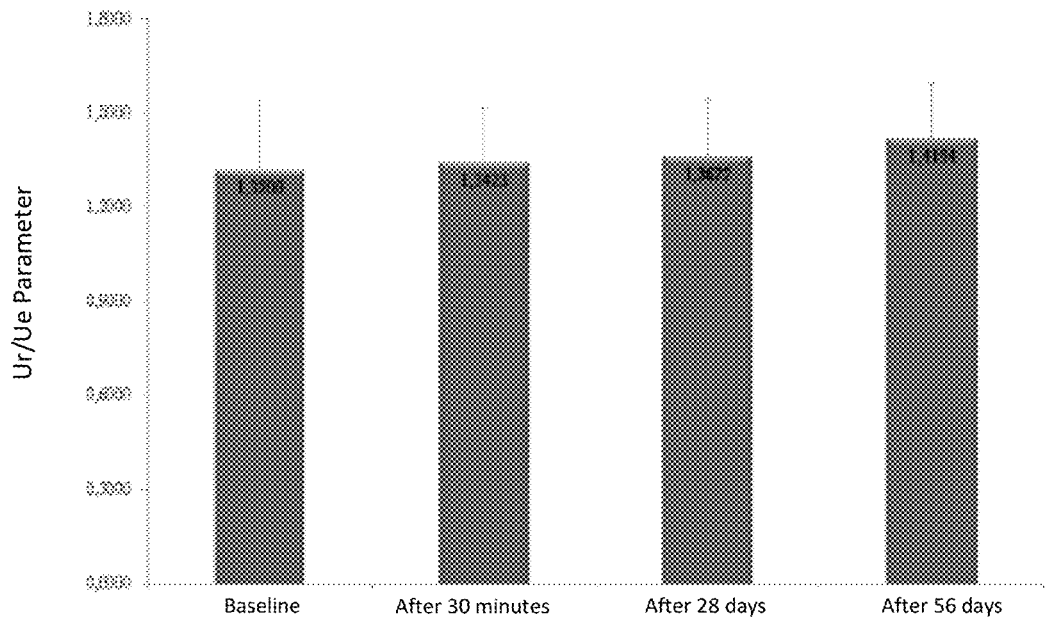

The graph of FIG. 1 shows the mean values of the Ur/Ue parameter obtained in the beginning of the study, 30 minutes after the first application, after 28 and 56 days of home use of the product being investigated.

Figure 2:
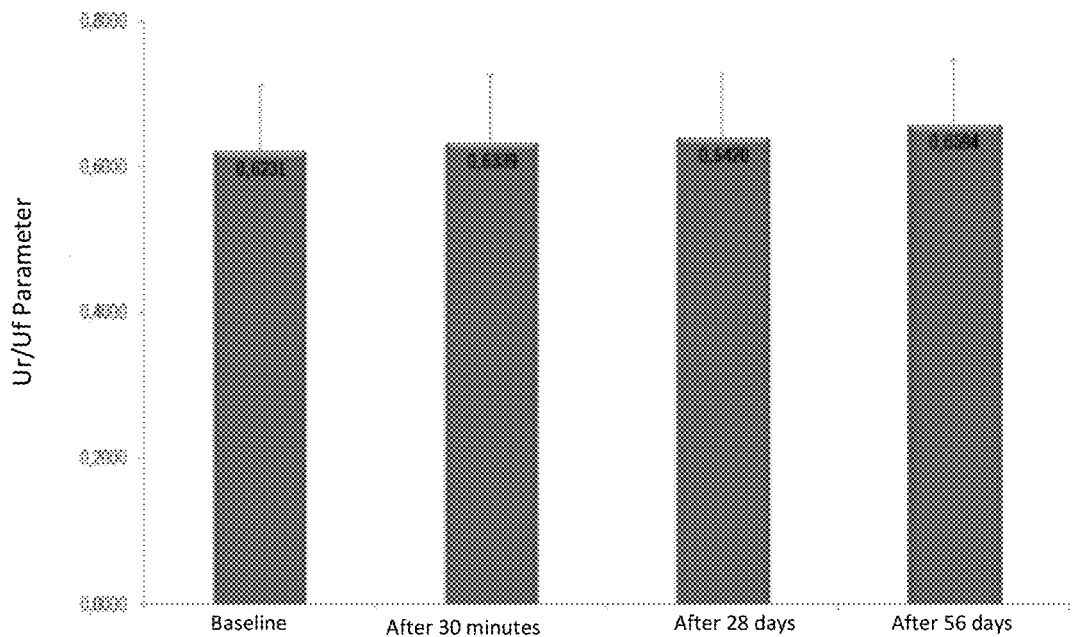

The graph of FIG. 2 shows the mean values of the Ur/Uf parameter obtained in the beginning of the study, 30 minutes after the first application, after 28 and 56 days of home use of the product being investigated.

Example 3. In Vivo Evaluation of the Increase in the Synthesis of Collagen by DRS 20 survey participants have completed the study. Average Age: 46±12 years.) There were no reports or evidence of adverse reaction during the study.

Upon enrollment of the participants in the study, they were instructed to discontinue the use of any topical products on the face for up to 72 hours prior to the beginning of the study. On the first day of the study, the survey participants who attended the laboratory were given clarifications by the main investigator on the study procedures, ethical and legal aspects, risks and benefits of the study procedure, medical support, reimbursement of participation costs and were asked to sign two copies of the TCLE. After staying for 15 minutes in an acclimatized room (22±2° C. and 50±5% RH), the baseline measurement (spectrum acquisition prior to the application of the product) was performed at the outer corner of the eye and the measurements were made randomly on the right and left sides of the survey participant. Spectra were obtained in the range of from 260 to 360 nm with emission at 380 nm using a 6-mm diameter optical-bifurcated probe coupled to Fluorolog—Jobin Yvan Horibe, Model FL3-12 with a xenon lamp. After the baseline measurement, the participants received the investigational product and instructions for using and completing the use log. The survey participants returned to the laboratory after 28, 56 and 90 days of use of the investigational product to repeat the measurement procedure, as performed on the first day of the study.

The composition according to the present invention was applied twice a day, once in the morning and once in the evening on clean and dry skin by massaging the product on the face until being completely absorbed.

According to the obtained results, it was possible to conclude that after 28, 56 and 90 days of continuous use of the investigational product a significant increase in collagen intensity was observed relative to the baseline skin condition. The product under investigation caused an increase in collagen intensity over the baseline skin condition of 3.1% after 28 days, 24.1% after 56 days and 26.1% after 90 days of continuous use.

The graph of FIG. 3 shows the mean values of the signal intensity referring to collagen, I340/I295 versus the time of study.

Example 4. Evaluation of the Efficacy of a Cosmetic Product Through the Efficacy Perceived by the Survey Participant and the Evaluation of Dermatological Clinical Efficacy Under Normal Use Conditions The survey participants were evaluated by a dermatologist in the beginning of the study (D0) to verify the inclusion and exclusion criteria and were also evaluated in the end of the study to verify possible reactions or discomforts experienced while using the product.

The included participants were clinically evaluated by the dermatologist for the initial state of the face skin and were later instructed to answer a self-assessment questionnaire on the initial state of the face skin (D0).

After inclusion and application of the initial questionnaire, the product was applied under supervision to all participants.

After the first application of the product, evaluations of perceived and clinical efficacy were performed through questionnaires 10 minutes after applying the product in the Institute (Immediate) and after 7, 14, 28 and 56 days (+/−2 days) of use of the product.

Participants were instructed to use the product at home according to the provided instructions for 56 days (+/−2 days).

70 female participants aged 40 to 70 years (average of 56 years) presenting wrinkles of grades II to V and apparent flaccidity of grades I to IV were included in the study.

Assessment of Perceived Efficacy:
An improvement in wrinkles (deep lines), expression lines/signs (fine lines), signs of aging, firmness, general appearance and facial harmony was observed in D14 and D56 as compared to D7;
An improvement in wrinkles (deep lines), expression lines/signs (fine lines), signs of aging, general appearance and facial harmony was observed in d28 as compared to D7;
An improvement in wrinkles (deep lines), expression lines/signs (fine lines), signs of aging, firmness and facial harmony was observed in D56 as compared to D14;
An improvement in expression lines/signs (fine lines), signs of aging, firmness, general appearance and facial harmony was observed in D56 as compared to D28.

Immediate:
72.4% of the participants perceived a tensor effect;
82.8% of participants reported improved overall appearance;
39.7% of the participants reported an improvement in the appearance of wrinkles/expression lines.

D7:
62% of the participants reported a reduction in wrinkles (deep lines);
66% of the participants reported a reduction in expression lines/signs (fine lines);
66% of the participants reported a reduction in the signs of aging (weather marks, spots, wrinkles/expression lines and sagging);
78% of the participants reported improved firmness;
91% of the participants reported an improvement in the overall appearance (bright, revitalized, rebalanced, healthy looking skin);
71% of the participants reported an improvement in facial harmony (improved facial contour).

D14:
71% of the participants reported a reduction in wrinkles (deep lines);
83% of the participants reported a reduction in expression lines/signs (fine lines);
83% of the participants reported a reduction in the signs of aging (weather marks, spots, wrinkles/expression lines and sagging);
91% of the participants reported an increase in skin firmness;
98% of the participants reported an improvement in the overall appearance (bright, revitalized, rebalanced, healthy looking skin);
86% of the participants reported an improvement in facial harmony (improved facial contour).

D28:
86% of the participants reported a reduction in wrinkles (deep lines);
88% of the participants reported a reduction in expression lines/signs (fine lines);
86% of the participants reported a reduction in the signs of aging (weather marks, spots, wrinkles/expression lines and sagging);
90% of the participants reported an increase in skin firmness;
98% of the participants reported an improvement in the overall appearance (bright, revitalized, rebalanced, healthy looking skin);
86% of the participants reported an improvement in facial harmony (improved facial contour).

D56:
93% of the participants reported a reduction in wrinkles (deep lines);
93% of the participants reported a reduction in expression lines/signs (fine lines);
90% of the participants reported a reduction in the signs of aging (weather marks, spots, wrinkles/expression lines and sagging);
91% of the participants reported an increase in skin firmness;
100% of the participants reported an improvement in the overall appearance (bright, revitalized, rebalanced, healthy looking skin);
91% of the participants reported an improvement in facial harmony (improved facial contour).

Assessment of Clinical Efficacy
Comparison with D0:
An improvement in firmness, facial harmony, overall appearance and healthy appearance was observed in times Immediate and D7 over D0;
An improvement in expression lines on the face, signs of aging, firmness, facial harmony, overall appearance and healthy appearance was observed at D14 as compared to D0;
An improvement in the degree of periorbital wrinkles, facial expression lines, signs of aging, degree of sagging, firmness, facial harmony, overall appearance and healthy appearance was observed at D28 and D56 as compared to D0.

Comparison with Immediate:
An improvement in facial harmony was observed at D7 as compared with
Immediate;
An improvement in the signs of aging, firmness, facial harmony, overall appearance and healthy appearance was observed at D14 as compared to Immediate;
An improvement in the degree of (periorbital) wrinkles, signs of aging, degree of sagging, firmness, facial harmony, overall appearance and healthy appearance was observed at D28 as compared to Immediate:

An improvement in the degree of (periorbital) wrinkles, facial expression lines, signs of aging, degree of sagging, firmness, facial harmony, overall appearance and healthy appearance was observed at D56 as compared to Immediate.

Comparison with D7:

An improvement in the signs of aging, firmness, facial harmony, overall appearance and healthy appearance was observed at D14 as compared to D7;

An improvement in the degree periorbital wrinkles, signs of aging, degree of sagging, firmness, facial harmony, overall appearance and healthy appearance was observed at D28 as compared to D7:

An improvement in the degree of periorbital wrinkles, facial expression lines, signs of aging, degree of sagging, firmness, facial harmony, overall appearance and healthy appearance was observed at D56 as compared to D7.

Comparison with D14:

An improvement in firmness, facial harmony, overall appearance and healthy appearance was observed in D28 as compared to D14;

An improvement in the degree of periorbital wrinkles, facial expression lines, signs of aging, degree of sagging, firmness, facial harmony, overall appearance and healthy appearance was observed at D56 as compared to D14.

Comparison with D28:

An improvement in the degree of periorbital wrinkles, facial expression lines, signs of aging, firmness, facial harmony, overall appearance and healthy appearance was observed at D56 as compared to D28.

Example 5. Evaluation of the Efficacy of a Cosmetic Product Through Instrumental Measurements Under Normal Use Conditions The survey participants were evaluated by a dermatologist in the beginning of the study (T0) to verify the inclusion and exclusion criteria and were also evaluated in the end of the study to verify possible reactions or discomforts experienced while using the product.

After the initial medical evaluation images of the periorbital, nasogenian, and frontal regions were obtained using Optical 3D Skin Measuring Device PRIMOS Compact 5.075. The obtained images of the periorbital and nasogenian regions were performed randomly.

After acquisition of the initial images the product was applied under supervision to all participants.

New images using Optical 3D Skin Measuring Device PRI MOS Compact 5.075 were performed 15 minutes after application of the product (Immediate) and after 7, 14, 28 and 56 days (+1-2 days) of use of the product.

Participants were instructed to use the product at home according to the provided instructions for 56 days (+1-2 days).

The participants were allowed to rest in a temperature- and relative humidity-controlled room (20° C.±2° C. and 50%±5 RH) for 30 minutes prior to the initial measurements and while performing the measurements.

29 female participants aged 32 to 69 years (average of 58 years) presenting wrinkles of grades II to V and apparent flaccidity of grades II to IV were included in the study.

Assessment of Cutaneous Relief—Primos

Periorbital Region:

The product caused a reduction in wrinkle volume after seven, fourteen, twenty-eight and fifty-six days of use;

The product caused a reduction in the average roughness (Ra) and average depth (Rz) of wrinkles after fifty-six days of use;

The product caused a reduction in rippling (Wt) of the wrinkles immediately after application of the product and after fifty-six days of use;

The product caused a reduction in wrinkle depth after fourteen, twenty-eight and fifty-six days of use;

The product caused a reduction in wrinkle texture after fifty-six days of use.

Nasogenian Region:

The product caused a reduction in the average roughness, average depth and maximum roughness of wrinkles after seven, fourteen, twenty-eight and fifty-six days of use.

The product caused a reduction in rippling of the wrinkles after seven and fourteen days of use;

The product caused a reduction in wrinkle texture after fifty-six days of use.

Frontal Region:

The product caused a reduction in volume, average roughness, average depth, maximum roughness, rippling and depth of the wrinkles after twenty-eight and fifty-six days of use; and The product caused a reduction in wrinkle texture after seven and fifty-six days of use.

The person skilled in the art, by means of the teachings of the text and examples disclosed herein, will readily appreciate the advantages of the invention and will propose equivalent embodiment variations and alternatives without departing from the scope of the invention as defined in the so appended claims.

The invention claimed is:

1. An anti-aging cosmetic composition, wherein the composition is a serum comprising:
    a) at least one antioxidant selected from the group consisting of butylated hydroxytoluene (BHT), tocopherol acetate, natural plant extracts, and mixtures thereof;
    b) at least one humectant selected from the group consisting of glycerol, glycols, sorbitol, mannitol, and mixtures thereof;
    c) a combination of *Hymenaea courbaril* extract and a mixture of unfermented *Paeonia albiflora* root extract/phenoxyethanol/ethylhexylglycerin;
    d) at least one emulsifier selected from the group consisting of polyethylene glycol (PEG)-40 hydrogenated castor oil, glyceryl citrate, potassium cetyl phosphate, PEG-100, acrylates, xanthan gum, cetearyl alcohol, mixture of glyceryl stearate/PEG-100, and mixtures thereof; and
    e) cosmetically acceptable carriers.

2. The composition of claim 1, wherein the at least one antioxidant is butylated hydroxytoluene (BHT).

3. The composition of claim 1, wherein the at least one humectant is glycerol.

4. The composition of claim 1, wherein the at least one emulsifier is PEG-40 hydrogenated castor oil.

5. The composition of claim 1, further comprising a viscosity donor selected from xanthan gum, carbopol, a mixture of hydroethylacrylate/sodium acryloyldimethyltaurate copolymer/squalane/polysorbate 60, and mixtures thereof.

6. The composition of claim 5, wherein the viscosity donor is xanthan gum.

\* \* \* \* \*